United States Patent
Cunningham et al.

(10) Patent No.: US 6,498,248 B1
(45) Date of Patent: Dec. 24, 2002

(54) LOW TEMPERATURE NON-CRYSTALLIZING LIQUID XYLITOL COMPOSITIONS AND CO-HYDROGENATION PROCESSES FOR MAKING SAME

(75) Inventors: Mary Lou Cunningham, Wilmington, DE (US); Charles E. Kuenzle, Newark, DE (US); Marguerite Yang, Hockessin, DE (US); Peter Jamieson, New Castle, DE (US)

(73) Assignee: SPI Polyols, Inc., New Castle, DE (US)

( * ) Notice: Subject to any disclaimer, the term of this patent is extended or adjusted under 35 U.S.C. 154(b) by 0 days.

(21) Appl. No.: 09/392,943

(22) Filed: Sep. 9, 1999

Related U.S. Application Data

(60) Provisional application No. 60/099,748, filed on Sep. 10, 1998.

(51) Int. Cl.[7] .............................. C07H 1/00; C13F 1/02; A23G 3/00
(52) U.S. Cl. ........................... 536/128; 426/658; 127/58
(58) Field of Search ........................ 536/128, 1.1, 124; 127/58; 579/23; 426/408; 926/658

(56) References Cited

U.S. PATENT DOCUMENTS

| | | | |
|---|---|---|---|
| 5,096,820 A | 3/1992 | Leleu et al. | 435/158 |
| 5,144,024 A | 9/1992 | Pepper | 536/128 |
| 5,728,225 A | 3/1998 | Duflot et at. | 127/29 |
| 5,773,604 A | 6/1998 | Lefevre et al. | |

FOREIGN PATENT DOCUMENTS

| | | |
|---|---|---|
| DE | 1058038 | 5/1959 |
| EP | 421 882 | 10/1990 |

OTHER PUBLICATIONS

Anonymous: "Lagereigenschaften Verbessert: Praktische Aspekte Der Herstellung von Zuckerfreiem Kaugummi Auf Basis Sorbit" Süsswaren, vol. 22, No. 7, 1978, pp. 44–58, XP002127945 tables 5, 9.

"Storage Properties IMproved, Practical Aspects of the Production of Sugar–Free Chewing Gum on the basis of Sorbitol" presented by E. Thieme upon the occasion of the International Chewing Gum Seminar at the Central Technical School in Solingen, Germany from Apr. 10 to 12, XP002127945, 1978.

*Primary Examiner*—Elli Peselev
(74) *Attorney, Agent, or Firm*—Connolly Bove Lodge & Hutz LLP

(57) ABSTRACT

A liquid xylitol composition that is non-crystallizing at low temperatures comprising, at between about 65 and about 90 weight percent dry solids, xylitol, in an amount between about 65 and about 90 weight percent of the dry solids, and sorbitol, in an amount between about 10 and about 35 weight percent of the dry solids. This liquid xylitol composition is preferably non-crystallizing at between about 0° C. and about 10° C. A process for producing liquid xylitol compositions, comprising co-hydrogenating a sugar syrup mixture comprising a sugar syrup having a dextrose equivalence (DE) of between about 20 DE and about 99 DE, in an amount between about 5 and about 35 weight percent of the mixture, and xylose, in an amount between about 65 and about 95 weight percent of the mixture. This process may be used to produce liquid xylitol compositions that are non-crystallizing at low temperatures.

7 Claims, No Drawings

LOW TEMPERATURE NON-CRYSTALLIZING LIQUID XYLITOL COMPOSITIONS AND CO-HYDROGENATION PROCESSES FOR MAKING SAME

This application is related to provisional application No. 60/099,748 filed Sep. 10, 1998 which is incorporated by reference in its entirety for all useful purposes.

BACKGROUND OF THE INVENTION

1. Field of the Invention

The present invention relates to xylitol compositions, and in particular, to liquid xylitol compositions that are non-crystallizing at low temperatures. The invention also relates to a co-hydrogenation process for producing liquid xylitol compositions, and a co-hydrogenation process for producing liquid xylitol compositions that are non-crystallizing at low temperatures.

2. The Related Art

The confectionary industry has long made use of xylitol as an ingredient in popular consumer products, such as chewing gums and candies. Xylitol has a sweet taste, a cooling effect in its crystalline form, and is non-cariogenic. The latter property provides a beneficial advantage of using xylitol, instead of sugar, as a sweetening agent. In fact, in some European countries and Canada, it is believed that xylitol actually repairs tooth decay. More recently, oral care companies also have begun to include xylitol in product formulations for toothpastes, mouthwashes, rinses, and the like.

Xylitol has been shown in many studies in countries outside the United States to have positive health benefits from reducing ear infections to recalcification of teeth. Many oral care and food manufacturers are exploring means to incorporate xylitol into their products.

Developers and manufacturers want the xylitol that they have incorporated into their products to remain in solution form. Many food products are stored at refrigerated and frozen storage temperatures, intentionally and unintentionally.

Xylitol is a sweetner that is as-sweet as sucrose. Crystalline xylitol, though, has a large negative heat of solution of −36.7 cal/g. When xylitol crystallizes in a product, the flavor profile changes and the product becomes cooling in the mouth, an objectionable characteristic in many products, such as toothpaste and fruit filings.

In many of its current applications in the confectionary and oral care industries, xylitol is employed in its crystalline (or dry) form. However, there are several disadvantages to using crystalline xylitol. Crystalline xylitol, being hygroscopic, quickly absorbs moisture and hardens, thereby making it difficult to handle. Also, the use of crystalline xylitol to produce an end product provides an added cost to that end product, since crystalline xylitol itself and its manufacturing process is expensive.

Recently, liquid xylitol has been proposed as an alternative to crystalline xylitol. The benefits of liquid xylitol are primarily in ease of handling and also potentially in cost, if the use of crystalline xylitol is avoided. Unfortunately, liquid xylitol has a tendency to crystallize out of solution, particularly at high concentrations on a dry solids basis. This makes it difficult to store liquid xylitol. Furthermore, the quality of end products can be diminished significantly. In oral care applications, for example, a crystallizing liquid xylitol will crystallize out of toothpaste and plug up tube orifices or pumps, or crystallize in a bottle or around a bottle cap in the case of rinses or mouthwashes.

U.S. Pat. No. 5,144,024 (the '024 patent) discloses a non-crystallizing liquid xylitol composition having a dry solids content of 60–80%, wherein the dry solids are comprised of 50–90% xylitol and 10–50% non-xylitol monomeric or dimeric polyols. The non-xylitol polyols are selected from maltitol, sorbitol, mannitol, glycerol and mixtures thereof. However, unlike the present invention, the '024 patent does not teach or suggest liquid xylitol compositions that are non-crystallizing at low temperatures. In fact, the '024 patent discloses that liquid xylitol/sorbitol formulations at 70% dry solids comprising 70% and 80% xylitol, and at 65% dry solids comprising 80% xylitol, will crystallize after only two weeks at both 5° C. and 10° C. Because products are often transported through and/or stored in cold environments, it is desirable to have a liquid xylitol that remains non-crystallizing at low temperatures.

The '024 patent teaches using a by-product stream from a xylitol crystallization process that is rich in xylitol, to make a liquid xylitol composition. In addition, the '024 patent discloses that liquid xylitol can be made by mixing a solution of pure xylitol with a solution containing other polyols. However, as discussed above, crystalline xylitol is expensive. It desired, therefore, to have process for making liquid xylitol that does not use crystalline xylitol or employ a xylitol crystallization step.

Heretofore, it has not been possible to achieve a liquid xylitol composition that is non-crystallizing at low temperatures preferably below about 10° C. It has also not been possible to provide a process for producing a liquid xylitol composition that does not use crystalline xylitol or employ a xylitol crystallization step.

SUMMARY OF THE INVENTION

An object of the present invention is to provide a liquid xylitol composition that is non-crystallizing at low temperatures of preferably less than about 10° C. for at least about 3 months and preferably at least about 4 months. In one aspect, a liquid xylitol composition that is non-crystallizing at low temperatures comprises, at between about 60 and about 95% and preferably between about 65 and about 90 weight percent dry solids, xylitol, in an amount between about 60 to about 90 weight percent and preferably about 65 and about 90 weight percent of the dry solids, and sorbitol, in an amount between about 10 and about 40 weight percent and preferably between about 10 and about 35 weight percent of the dry solids. This liquid xylitol composition is preferably non-crystallizing at temperatures below about 10° C., and more preferably between about 0° C. and about 10° C.

Another object of this invention is to provide a co-hydrogenation process for producing liquid xylitol compositions. In one aspect, the process comprises co-hydrogenating a sugar syrup mixture comprising a sugar syrup having a dextrose equivalence (DE) of between about 20 DE and about 99 DE, in an amount between about 5 and about 35 weight percent of the mixture, and xylose, in an amount between about 65 and about 95 weight percent of the mixture. The co-hydrogenating step takes place preferably at a temperature of between about 120° C. and about 170° C., and a hydrogen pressure of between about 200 psi and about 2000 psi, for between about 90 and about 180 minutes.

A further object of this invention is to provide a co-hydrogenation process for producing liquid xylitol compositions that are non-crystallizing at low temperatures. In one aspect, the process comprises co-hydrogenating a sugar syrup mixture comprising a sugar syrup having a dextrose equivalence (DE) of between about 20 DE and about 99 DE, in an amount between about 5 and about 35 weight percent of the mixture, and xylose, in an amount between about 65 and about 95 weight prevent of the mixture, to produce a liquid xylitol composition that is non-crystallizing at low temperatures. The liquid xylitol composition produced by this co-hydrogenation process is preferably non-crystallizing at between about 0° C. and about 10° C., and preferably comprises, at between about 65 and about 90 weight percent dry solids, xylitol, in an amount between about 65 and about 90 weight percent of the dry solids, and sorbitol, in an amount between about 10 and about 35 weight percent of the dry solids. The co-hydrogenating step takes place preferably at a temperature between about 120° C. and about 170° C., and a hydrogen pressure between about 200 psi and about 2000 psi, for between about 90 and about 180 minutes.

I have found that co-hydrogenated xylitol/sorbitol produced with hydrogenation process creates a means of introducing xylitol into a product, without the difficulties of incorporating crystalline xylitol into the product. Xylitol (in crystalline form) is difficult to work with because of it's hygroscopic nature. Xylitol lumps during storage in its dry form and during incorporation. Xylitol (in its dry form) will crystallize out of products at low temperatures, creating objectionable textures in an ingestible composition such as but not limited to oral care products such as, but not limited to, toothpaste, mouth wash and embedded in the coating of dental floss and food products, such as but not limited to a form of confection, chewing gum and fruit syrup. The crystals will dissolve in the mouth and create an objectionable mouth sensation. Other co-hydrogenated xylitol/sorbitol sources can also crystallize out at cool temperatures, also causing objectionable textures and a cooling mouth sensation.

Other aspects of the present invention will be better understood and advantages thereof more apparent in view of the following detailed description of the preferred embodiments.

DETAILED DESCRIPTION OF THE PREFERRED EMBODIMENTS

One embodiment of the invention is a non-crystallizing liquid composition which comprises dry solids and the composition is non-crystallizing at temperatures below about 10° C. The liquid xylitol compositions in accordance with this invention comprise preferably between about 65 and about 90 weight percent dry solids, more preferably between about 65 and about 80 weight percent dry solids, and even more preferably between about 70 and about 80 weight percent dry solids.

A liquid xylitol composition that is non-crystallizing at low temperatures comprises both a xylitol component and a non-xylitol polyol component.

The xylitol component comprises, on a dry solids basis, preferably between about 65 and about 90 weight percent of the dry solids, more preferably between about 65 and about 80 weight percent of the dry solids, and even more preferably between about 65 and about 75 weight percent of the dry solids.

The non-xylitol polyol component comprises at least one non-xylitol polyol selected from the group consisting of sorbitol, mannitol, maltitol, maltitriitol, and other larger chain sugar alcohols (i.e., DP4 and greater). The non-xylitol polyol component comprises, on a dry solids basis, preferably between about 10 and about 35 weight percent of the dry solids, more preferably between about 20 and about 35 weight percent of the dry solids, and even more preferably between about 25 and about 35 percent of the dry solids. In a preferred embodiment, the non-xylitol polyol component comprises non-xylitol monomeric polyols. In a more preferred embodiment, the non-xylitol polyol component comprises sorbitol.

A liquid xylitol composition that is non-crystallizing at low temperatures is non-crystallizing at a temperature of below about 10° C., preferably between about 0° C. and about 10° C., more preferably between about 0° C. and about 5° C., and even more preferably between about 0° C. and about 3° C. The liquid xylitol composition is non-crystallizing for preferably at least about 2 months, more preferably at least about 3 months, and even more preferably at least about 4 months.

A process for producing a liquid xylitol composition that does not use crystalline xylitol or employ a xylitol crystallization step, comprises a co-hydrogenation step. The co-hydrogenation step comprises hydrogenating a sugar syrup mixture. The sugar syrup mixture preferably comprises both xylose and a sugar syrup component. The xylose can be in the form of either a syrup, a solid, or a combination thereof. The sugar syrup component comprises preferably at least one sugar syrup that functions as a source for non-xylitol polyols, and even more preferably at least one sugar syrup that functions as a source for non-xylitol monomeric polyols. Sugar syrups may include dextrose (as a source for sorbitol), maltose (as a source for maltitol), and other starch hydrolysates as sources for larger chain sugar alcohols (e.g., DP3 and greater) In a preferred embodiment, the sugar syrup component comprises dextrose.

Any conventional xylose and sugar syrups may be employed in the sugar syrup mixture. The xylose should have a xylose assay of preferably about 92%, more preferably about 95%, and even more preferably about 99%. Any sugar syrup employed should have a dextrose equivalence (DE) of preferably between about 20 DE and about 99 DE, more preferably between about 43 DE and about 99 DE, and even more preferably about 99 DE. A preferred source of xylose is Cultor Food Science/Xyrofin (New York, N.Y.). Preferred sugar syrup sources include A.E. Staley Manufacturing Company (Decatur, Ill.) and Com Product, CPC International (Argo, Ill.).

The xylose comprises preferably between about 65 and about 95 weight percent of the sugar syrup mixture, more preferably between about 65 and about 85 weight percent of the sugar syrup mixture, and even more preferably between about 65 and about 75 weight percent of the sugar syrup mixture. The sugar syrup component comprises preferably between about 5 and about 35 weight percent of the sugar syrup mixture, more preferably between about 15 and about 35 weight percent of the sugar syrup mixture, and even more preferably between about 25 and about 35 weight percent of the sugar syrup mixture.

The co-hydrogenation step is conducted at a temperature of preferably between about 120° C. and about 170° C., more preferably between about 120° C. and about 150° C., and even more preferably between about 140° C. and about 150° C.

Co-hydrogenation is achieved by heating the polyol syrup mixture in an elevated hydrogen pressure environment. The hydrogen pressure is preferably between about 200 psi and about 2000 psi, more preferably between about 200 psi and about 550 psi, and even more preferably between about 200 psi and about 250 psi. Another preferred hydrogen pressure is between about 550 psi and about 2000 psi.

Catalysts may be employed during the co-hydrogenation step. The catalyst comprises preferably a nickel catalyst, more preferably a sponge nickel catalyst, and even more preferably a molybdenum promoted sponge nickel catalyst. A preferred brand of catalyst is A7063 (available from Activated Metals and Chemicals, Inc., Sevierville, Tenn.).

Any conventional hydrogenation equipment may be used to conduct co-hydrogenation processes according to this invention. The residence time for carrying out the co-hydrogenation step is preferably between about 90 minutes about 180 minutes, more preferably between about 120 minutes and about 150 minutes, and even more preferably about 150 minutes.

Liquid xylitol compositions that are non-crystallizing, in accordance with this invention, may be produced by co-hydrogenation processes in accordance with this invention.

resin (available from Sybron, Birmingham, N.J.). The ion exchange sample was evaporated to about 70 weight percent dry solids.

Table 1 indicates the xylitol and sorbitol percentages of each ion-exchanged sample. The notation "d.b." indicates dry solids basis.

TABLE 1

| Sample | Dextrose % | Xylose % | Catalyst (A7063) % | cycle | Temp. °C. | Pressure psi | Time minutes | HPLC % xylitol | % sorbitol |
|---|---|---|---|---|---|---|---|---|---|
| 1.1 | 65 | 35 | 5 | 1 | 140 | 250 | 150 | 32.95 d.b. | 62.48 d.b. |
| 1.2 | 65 | 35 | Recycle +1% | 2 | 140 | 250 | 150 | 33.29 d.b. | 62.58 d.b. |
| 1.3 | 65 | 35 | Recycle +1% | 2 | 140 | 250 | 150 | 33.15 d.b. | 62.22 d.b. |
| 1.4 | 65 | 35 | Recycle +1% | 3 | 140 | 250 | 150 | 33.57 d.b. | 62.53 d.b. |
| 1.5 | 65 | 35 | Recycle +1% | 3 | 140 | 250 | 150 | 33.16 d.b. | 61.98 d.b. |
| 1.6 | 65 | 35 | Recycle +1% | 4 | 140 | 250 | 150 | 33.65 d.b. | 62.53 d.b. |
| 1.7 | 65 | 35 | Recycle +1% | 4 | 140 | 250 | 150 | 33.23 d.b. | 61.69 d.b. |

EXAMPLES

Examples I–IV comprise preferred embodiments of this invention. Example V is a comparative example involving preferred embodiments of this invention. All references to percentages and percent values in the Examples are references to weight percentages and weight percent values, unless otherwise indicated. The present invention is not limited to these Examples.

EXAMPLE I

Referring to Table 1, Samples 1.1 through 1.7 were made by co-hydrogenation of sugar mixtures comprising 35% xylose and 65% dextrose on a dry solids bases at 50 weight percent dry solids. All sugar mixtures were combinations of crystalline xylose and 99 DE dextrose syrup.

The catalyst employed in Example I was a sponge nickel catalyst type A7063 (available from Activated Metals and Chemicals, Inc., Sevierville, Tenn.). This is a molybdenum promoted catalyst, typically containing approximately 1.5% molybdenum and 85% nickel. As shown in Table 1, the initial catalyst charge was 5% on a dry solids basis. For each subsequent sample, the same catalyst was recycled and an additional percentage amount was added to compensate for physical losses and losses in activity.

Samples 1.1 through 1.7 were each produced in a set of Parr rocking reactors (total volume 3 L), to which the standard charge weight was 850 grams. The operating conditions of temperature, hydrogen pressure, and residence time are indicated in Table 1.

After reaction was complete, each sample was cooled, pressure was relieved and the reaction mass was discharged to a graduated cylinder to allow the nickel catalyst to settle to the bottom. Typically, each sample was allowed to settle overnight. After catalyst settling, the supernant liquid was decanted off the top and filtered through a Buchner funnel to remove fines. The sample was then ion exchanged through AMBERLITE A200 strong acid cation resin (available from Rohm & Haas, Philadelphia, Pa.) and either Mitsubishi RDA 416 strong base anion resin (available from Mitsubishi Chemical, White Plains, N.Y.) or A651 strong base anion

EXAMPLE II

Referring to Table 2, Samples 2.1 through 2.6 were made by co-hydrogenation of sugar mixtures comprising 50% xylose and 50% dextrose on a dry solids basis at 50 weight percent dry solids. All sugar mixtures were combinations of crystalline xylose and 99 DE dextrose syrup.

The catalyst employed in Example II was a continuing recycle of the same recycled sponge nickel catalyst type A 7063 employed in Example I. As shown in Table 2, for each sample, the catalyst was recycled and an additional percentage amount was added to compensate for physical losses and losses in activity.

Samples 2.1 through 2.6 were each produced in a set of Parr rocking rectors (total volume 3 L), to which the standard charge weight was 850 grams. The operating conditions of temperature, hydrogen pressure, and residence time are indicated in Table 2.

After reaction was completed, each sample was cooled, pressure was relieved and the reaction mass was discharged to a graduated cylinder to allow the nickel catalyst to settle to the bottom. Typically, each sample was allowed to settle overnight. After catalyst settling, the supernatant liquid was decanted off the top and filtered through a Buchner funnel to remove fines. The sample was then ion exchanged through AMBERLITE A200 strong acid cation resin (available from Rohm & Haas, Philadelphia, Pa.) and either Mitsubishi RDA 416 strong base anion resin (available from Mitsubishi Chemical, White Plains, N.Y.) or A651 strong base anion resin (available from Sybron, Birmingham, N.J.). The ion exchanged sample was evaporated to about 70 weight percent dry solids.

Table 2 indicates the xylitol and sorbitol percentages of each ion-exchanged sample. The notation "d.b." indicates dry solids basis. Otherwise, the percentages are "as is" (i.e., including percent water).

TABLE 2

| Sample | Dextrose % | Xylose % | Catalyst (A7063) % | cycle | Temp. °C. | Pressure psi | Time minutes | HPLC % xylitol | % sorbitol |
|---|---|---|---|---|---|---|---|---|---|
| 2.1 | 50 | 50 | Recycle +10% | 5 | 140 | 250 | 150 | 25.51 | 25.91 |
| 2.2 | 50 | 50 | Recycle +10% | 5 | 140 | 250 | 150 | 24.4 | 24.7 |
| 2.3 | 50 | 50 | Recycle +1% | 6 | 140 | 250 | 150 | 25.35 | 25.55 |
| 2.4 | 50 | 50 | Recycle +1% | 6 | 140 | 250 | 150 | 24.45 | 24.55 |
| 2.5 | 50 | 50 | Recycle +1% | 7 | 140 | 250 | 150 | 48.15 d.b. | 47.67 d.b. |
| 2.6 | 50 | 50 | Recycle +1% | 7 | 140 | 250 | 150 | 47.93 d.b. | 47.29 d.b. |

EXAMPLE III

Referring to Table 3, Samples 3.1 through 3.6 were made by co-hydrogenation of sugar mixtures comprising 65% xylose and 35% dextrose on a dry solids basis at 50 weight percent dry solids. All sugar mixtures were combinations of crystalline xylose and 99 DE dextrose syrup.

AMBERLITE A200 strong acid cation resin (available from Rohm & Haas, Philadelphia, Pa.) and either Mitsubishi RDA 416 strong base anion resin (available from Mitsubishi Chemical, White Plains, N.Y.) or A651 strong base anion resin (available from Sybron, Birmingham, N.J.). The ion exchanged sample was evaporated to about 70 weight percent dry solids.

TABLE 3

| Sample | Dextrose % | Xylose % | Catalyst (A7063) % | cycle | Temp. °C. | Pressure psi | Time minutes | HPLC % xylitol | % sorbitol |
|---|---|---|---|---|---|---|---|---|---|
| 3.1 | 35 | 65 | Recycle +1% | 8 | 140 | 250 | 150 | | |
| 3.2 | 35 | 65 | Recycle +1% | 8 | 140 | 250 | 150 | | |
| 3.3 | 35 | 65 | Recycle +1% | 9 | 140 | 250 | 150 | | |
| 3.4 | 35 | 65 | Recycle +1% | 9 | 140 | 250 | 150 | | |
| 3.5 | 35 | 65 | Recycle +1% | 10 | 140 | 250 | 150 | | |
| 3.6 | 35 | 65 | Recycle +1% | 10 | 140 | 250 | 150 | | |

The catalyst employed in Example III was a continuing recycle of the same recycled sponge nickel catalyst type A7063 employed in Example II. As shown in Table 3, for each sample, the catalyst was recycled and an additional percentage amount was added to compensate for physical losses and losses in activity.

Samples 3.1 through 3.6 were each produced in a set of Parr rocking reactors (total volume 3 L), to which the standard charge weight was 850 grams. The operating conditions of temperature, hydrogen pressure, and residence time are indicated in Table 3.

A liquid xylitol composition that is non-crystallizing at low temperatures is non-crystallizing at a temperature of preferably between about 0° C. and about 10° C.

After reaction was complete, each sample was cooled, pressure was relieved and the reaction mass was discharged to a graduated cylinder to allow the nickel catalyst to settle to the bottom. Typically, each sample was allowed to settle overnight. After catalyst settling, the supernant liquid was decanted off the top and filtered through a Buchner funnel to remove fines. The sample was then ion exchanged through

EXAMPLE IV

Table 4 contains Blends 4.1, 4.2, and 4.3. Blend 4.1 was made from a combination of Samples 1.2 through 1.7. Blend 4.2 was made from a combination of Samples 2.1 through 2.6. Blend 4.3 was made from a combination of Samples 3.1 through 3.6.

Table 4 indicates the water, xylitol and sorbitol weight percentages of each Blend. The notation "d.b." indicates dry solids basis.

TABLE 4

| Blend | % Water | HPLC % xylitol | % sorbitol |
|---|---|---|---|
| 4.1 | 30.4 | 33.36 d.b. | 61.8 d.b. |
| 4.2 | 32.5 | 47.68 d.b. | 47.55 d.b. |
| 4.3 | 30.2 | 61.84 d.b. | 33.65 d.b. |

EXAMPLE V

Comparative Blends A1 through A3 and B1 through B3 represent three xylitol/sorbitol ratios, as shown in Table 5.

Comparative Blends A1 through A3 were made by combining dry xylitol, dry sorbitol and water. Comparative Blends B1 through B3 were made by combining dry xylitol and liquid sorbitol. Each of the six Comparative Blends has a dry solids content of approximately 70 weight percent.

These Comparative Blends were set up for a stability test at room temperature (approximately about 22–30° C.) and at 3° C. Blends 4.1 through 4.3 were also set up for stability under the same temperature conditions.

After 2 weeks, Comparative Blends A3 and B3 (containing approximately 65% xylitol d.b.) showed crystal growth at 3° C. Blend 4.3 (containing approximately 62% xylitol d.b.) showed no crystal growth at 3° C. After three months, Blend 4.3 has yet to show any crystal growth at 3° C. None of the other comparative blends or blends showed crystal growth at either room temperature or at 3° C.

TABLE 5

| SAMPLE | % xylitol d.b. | % sorbitol d.b. | Stability Test Room Temp | 3° C. |
|---|---|---|---|---|
| Comparative Blend A1 | 35 | 65 | — | — |
| Comparative Blend B1 | 35 | 65 | — | — |
| Comparative Blend A2 | 50 | 50 | — | — |
| Comparative Blend B2 | 50 | 50 | — | — |
| Comparative Blend A3 | 65 | 35 | — | 2 weeks |
| Comparative Blend B3 | 65 | 35 | — | 2 weeks |
| Blend 4.1 | 33.36 | 61.8 | — | — |
| Blend 4.2 | 47.68 | 47.55 | — | — |
| Blend 4.3 | 61.84 | 33.65 | — | — |

A comparison was made between comparison example 5-1 and example 5-2. The examples were identical except that comparison example 5-1 was not co-hydrogentated while example 5-2 was co-hydrogenated. The examples contain 70% solids (65 xylitol/35 sorbitol) solution prepared from crystalline material. The co-hydrogenated example had unexpectedly superior properties as discussed below.

Examples 5-1 and 5-2 were a toothpaste formulation with 65% Xylitol/35% Sorbitol and contained the following ingredients:

| Ingredients | weight (g) | percentage |
|---|---|---|
| Glycerin | 300 | 15.03 |
| Carboxymethyl-cellulose | 26 | 1.30 |
| Sodium Saccharin | 14 | 0.70 |
| De-ionized water | 306 | 15.09 |
| 65% xylitol/35% sorbitol (70% solids solution) | 500 | 25.06 |
| Titanium oxide | 4 | 0.20 |
| Sodium Bicarbonate | 500 | 25.06 |
| Zeo-dent 115 | 300 | 15.04 |
| Peppermint flavor | 20 | 1.00 |
| Sodium Lauryl Sulfate | 30 | 1.50 |

The results were as follows:

1. Viscosity

The results demonstrated that the viscosity of comparison example 5-1 was higher by approximately <3% than example 5.2.

| time in seconds | Comparison Example 5-1 | Example 5-2 |
|---|---|---|
| 0 | 27.0 | 25.5 |
| 12 | 30.0 | 29.0 |
| 24 | 31.5 | 30.5 |
| 36 | 31.5 | 31.0 |
| 48 | 32.5 | 32.0 |
| 60 | 33.5 | 33.0 |
| 72 | 34.3 | 34.0 |

(Brookfield viscosity units)

| time in seconds | Comparison Example 5-1 | Example 5-2 |
|---|---|---|
| 0 | 135,000 | 127,500 |
| 12 | 150,000 | 145,000 |
| 24 | 157,500 | 152,500 |
| 36 | 157,500 | 155,000 |
| 48 | 162,500 | 160,000 |
| 60 | 167,500 | 165,000 |
| 72 | 171,250 | 170,000 |

(units converted into centipoise)

2. Color

The example 5-2 demonstrated toothpaste that had a more white color than comparison example 5-1. This was determined by the use of the Gardner "color meter".

| | standard | comparison example 5-1 | example 5-2 |
|---|---|---|---|
| L | 83.36 | 79.80 | 80.25 |
| a | −1.10 | −1.40 | −1.39 |
| B | 1.58 | 0.80 | 0.90 |
| CIE | 0.00 | 0.00 | 0.00 |

3. Cohesion

Example 5-2 demonstrated more cohesion than comparison example 5-1. This was determined by the use of the Instron.

| run # | Comparison Example 5-1 | Example 5-2 |
|---|---|---|
| 1 | 9.5 | 10.5 |
| 2 | 10.0 | 10.5 |
| 3 | 10.25 | 11.0 |

(units are in grams of force)

General Observations

Example 5-1 had less gloss than example 5-2.

Example 5-1 appeared to be not as white as example 5-2.

Example 5-1 appeared to skin where example 5-2 did not.

Example 6 illustrates the liquid xylitol composition being used in candy. Dry and liquid materials were used in an open pan. 10 grams of extra water were added to formulas A, C and E below to allow the dry materials to dissolve when they were heated. Extra water was not need, with the co-hydrogenated mixture. The co-hydrogenated mixture used in this example had a 70% level of solids and contained 65% xylitol and 35% sorbitol. The mixtures were heated over a gas flame until their weight revealed the loss of weight sufficient to make the cooked candy less than 5% moisture. Samples were then poured onto cooling pan and into plastic lined molds. Samples were evaluated over 48 hours.

| Formulas | | | |
|---|---|---|---|
| | Wet Formula | | Cooked Composition |
| A. | | | |
| Xylitol (Solid) | 95% | | 95% |
| Water | 5% | | 5% |
| Total | 100% | | 100% |
| B. | | | |
| Xylitol (Solid) | 48.8% | Xylitol | 80.9% |
| co-hydrogenated xylitol(65)/sorbitol(35) | 51.2% | Sorbitol | 14.0% |
| | | Water | 5.1% |
| Total | 100% | | 100% |
| C. | | | |
| Xylitol (Solid) | 81% | | 81% |
| Sorbitol (Solid) | 14% | | 14% |
| Water | 5% | | 5% |
| Total | 100% | | 100% |
| D. | | | |
| Xylitol (Solid) | 83.3% | Xylitol | 90.9% |
| co-hydrogenated xylitol(65)/sorbitol(35) | 16.7% | Sorbitol | 4.1% |
| | | Water | 5.0% |
| Total | 100% | | 100% |
| E. | | | |
| Xylitol (Solid) | 91% | | 91% |
| Sorbitol (Solid) | 4% | | 4% |
| Water | 5% | | 5% |
| Total | 100% | | 100% |

The results for each of formulas is as follows:

Formula A: Fastest crystal growth (less than one hour). The final cooled product is very hard and has very visible large crystals. The hard candy is not sticky.

Formula B: Second slowest crystal growth. The final cooled product is hard, homogeneous, and has much less noticeable crystals. The hard candy is not sticky.

Formula C: Slowest crystal growth. When the others samples were hard homogeneous after 24 hours, this sample was still greatly syrup with visible large crystals. The Candy is very sticky (even the crystallized part) after 24 hours, though hard and non-sticky after 72 hours.

Formula D: Faster crystal growth than Formula B and slower than Formula E. Final cooled product is hard, with slightly less visible crystals than Formula E. The hard candy is not sticky.

All of the formulas appear to have similar hardness after 72 hours.

In summary, the addition of co-hydrogenated xylitol allows the manufacturing of high xylitol candy with greater ease than with solid xylitol alone or with dry xylitol and dry sorbitol. The water in the co-hydrogenated material eliminates the need for added water to dissolve the polyols before cooking. The co-hydrogenated xylitol/non-xylitol polyol (such as but not limited to sorbitol) slows the crystallization down and yet allows for less noticeable, smaller crystals in the finished product. Just adding sorbitol and xylitol does not effect the crystal growth in the same way. The invention is not limited by the percentage of xylitol, thus co-hydrogenated xylitol/sorbitol at 35/65 ratio should perform with the same properties as that at the higher xylitol ratio.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent formulations and functions.

We claim:

1. A process for producing a liquid xylitol composition which comprises co-hydrogenating a xylose and a non-xylose sugar syrup which functions as a source for non-xylitol polyol and wherein the process does not use crystalline xylitol or employ a xylitol crystallization step.

2. The process as claimed in claim 1, wherein said non-xylitol polyol is a monomeric polyol.

3. The process as claimed in claim 1, wherein the co-hydrogenation is at a temperature below about 170° C. and a hydrogen pressure below about 2000 psi.

4. The process as claimed in claim 3, wherein the co-hydrogenation is at a temperature between about 120° C. to about 170° C. and a hydrogen pressure between about 200 psi to 2000 psi.

5. The process as claimed in claim 4, wherein the co-hydrogenation is at a temperature between about 120° C. to about 150° C. and a hydrogen pressure about 200 psi to about 550 psi.

6. The process as claimed in claim 5, wherein the co-hydrogenation is at a temperature between about 140° C. and 150° C. and a hydrogen pressure is between about 200 psi and about 250 psi.

7. The process as claimed in claim 1, wherein the non-xylose syrup is selected from the group consisting of sorbitol, mannitol, maltitol, maltitriitol and a mixture thereof.

* * * * *